(12) United States Patent (10) Patent No.: US 8,343,117 B1
Rosado (45) Date of Patent: Jan. 1, 2013

(54) COMBINATION CIGARETTE LIGHTER AND EYE DROP DEVICE

(76) Inventor: Michael Rosado, Miami, FL (US)

( * ) Notice: Subject to any disclaimer, the term of this patent is extended or adjusted under 35 U.S.C. 154(b) by 369 days.

(21) Appl. No.: 12/689,893

(22) Filed: Jan. 19, 2010

(51) Int. Cl.
*A61M 35/00* (2006.01)
*F23Q 2/32* (2006.01)

(52) U.S. Cl. ........................................ 604/295; 431/253

(58) Field of Classification Search .................. 431/253; 604/294–302
See application file for complete search history.

(56) References Cited

U.S. PATENT DOCUMENTS

| | | | |
|---|---|---|---|
| 1,793,899 A * | 2/1931 | Benforado | 150/116 |
| 1,846,763 A * | 2/1932 | Schaefer | 604/301 |
| D124,449 S * | 12/1940 | Flato | D10/31 |
| 2,358,955 A | 9/1944 | Weston | |
| D152,386 S * | 1/1949 | Zelenka | D3/209 |
| D157,038 S * | 1/1950 | Florman | D27/142 |
| 2,495,897 A * | 1/1950 | Kemp | 128/202.13 |
| 2,521,630 A * | 9/1950 | Florman | 422/293 |
| D163,534 S * | 6/1951 | Monturo | D27/142 |
| D184,636 S | 3/1959 | Pickerell et al. | |
| 2,987,439 A * | 6/1961 | Wittlinger | 424/45 |
| 3,170,462 A * | 2/1965 | Hall | 128/200.23 |
| 3,468,454 A * | 9/1969 | Joncas | 221/147 |
| 3,872,865 A * | 3/1975 | Casey | 604/302 |
| D248,448 S | 7/1978 | McClure et al. | |
| D254,151 S | 2/1980 | Wolff | |
| 4,230,224 A * | 10/1980 | Weeks | 206/87 |
| 4,515,556 A | 5/1985 | Vanelli | |
| 4,583,939 A | 4/1986 | Brickwedde | |
| 5,169,305 A * | 12/1992 | Kee | 431/253 |
| 5,271,730 A * | 12/1993 | Acacio da Silva | 431/253 |
| 5,346,132 A * | 9/1994 | Hahn et al. | 239/71 |
| 5,366,448 A | 11/1994 | Basilice et al. | |
| 5,454,657 A * | 10/1995 | Kim | 401/195 |
| 5,682,981 A * | 11/1997 | Sudborough | 206/38.1 |
| 5,927,272 A * | 7/1999 | Robertson | 126/699 |
| 6,056,539 A * | 5/2000 | Carlson | 431/253 |
| 6,336,917 B1 * | 1/2002 | Berke | 604/295 |
| D464,168 S * | 10/2002 | Reynolds et al. | D27/142 |
| 2001/0032652 A1 | 10/2001 | Ng | |
| 2002/0107492 A1 * | 8/2002 | Brach et al. | 604/296 |
| 2003/0078551 A1 * | 4/2003 | Hochrainer et al. | 604/295 |
| 2003/0211049 A1 * | 11/2003 | Gerassi | 424/48 |
| 2005/0261641 A1 * | 11/2005 | Warchol et al. | 604/294 |
| 2007/0108091 A1 * | 5/2007 | Stewart | 206/581 |

* cited by examiner

*Primary Examiner* — Melanie Hand
*Assistant Examiner* — Paula Craig

(57) ABSTRACT

A cigarette lighter device comprising a cigarette lighter component having a top end, a bottom end, and a butane reservoir disposed inside; an eye drop dispenser removably attached to the bottom end of the cigarette lighter component, wherein the eye drop dispenser has a reservoir for storing an eye drop fluid; a connecting tube fluidly connecting the reservoir to an aperture tip disposed at a first end of the eye drop dispenser; wherein the eye drop fluid can be squeezed from the reservoir out of the eye drop dispenser; a removable cap attached to the first end of the eye drop dispenser for temporarily preventing eye drop fluid from unintentionally exiting the eye drop dispenser.

4 Claims, 5 Drawing Sheets

COMBINATION CIGARETTE LIGHTER AND EYE DROP DEVICE

FIELD OF THE INVENTION

The present invention is directed to a cigarette lighter, more particularly to a cigarette lighter comprising an eye drop dispenser device.

BACKGROUND OF THE INVENTION

Cigarette smoke or smoke from other substances can often irritate one's eyes. The present invention features a novel device that combines a cigarette lighter and eye drops, which can provide a user with quick and easy access to eye drops.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
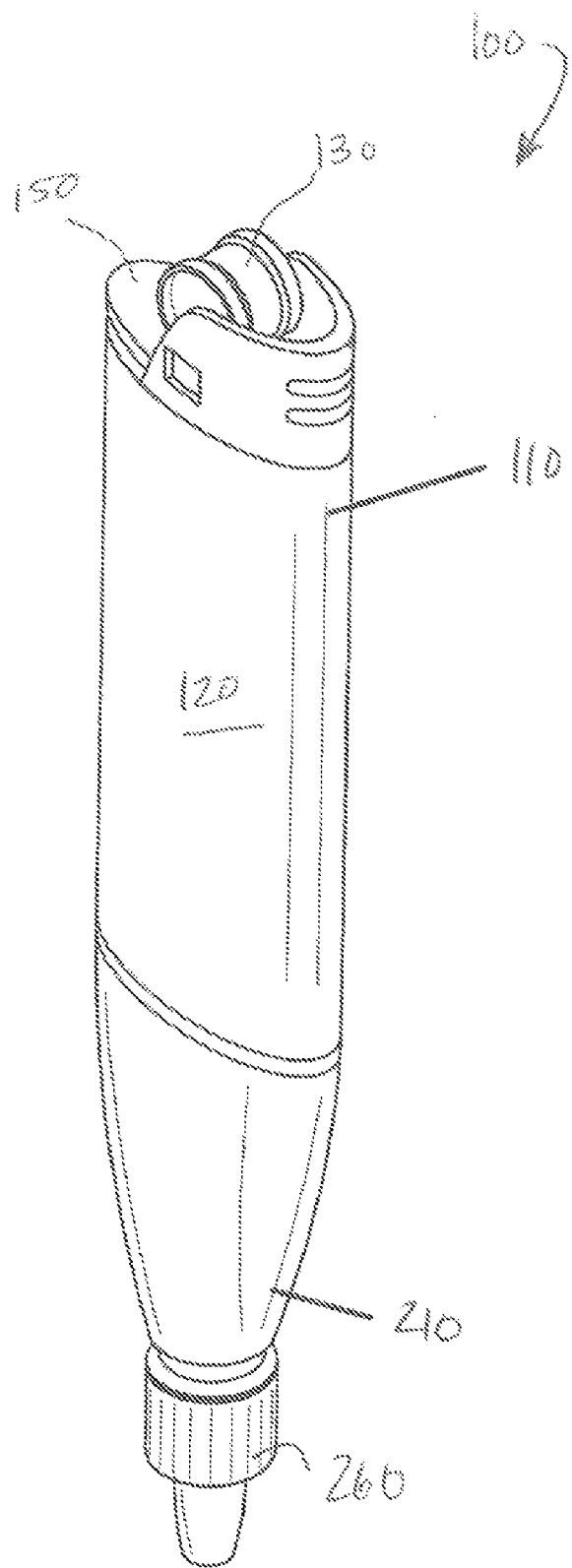
FIG. 1 is a top perspective view of the cigarette lighter device of the present invention.
Figure 2:
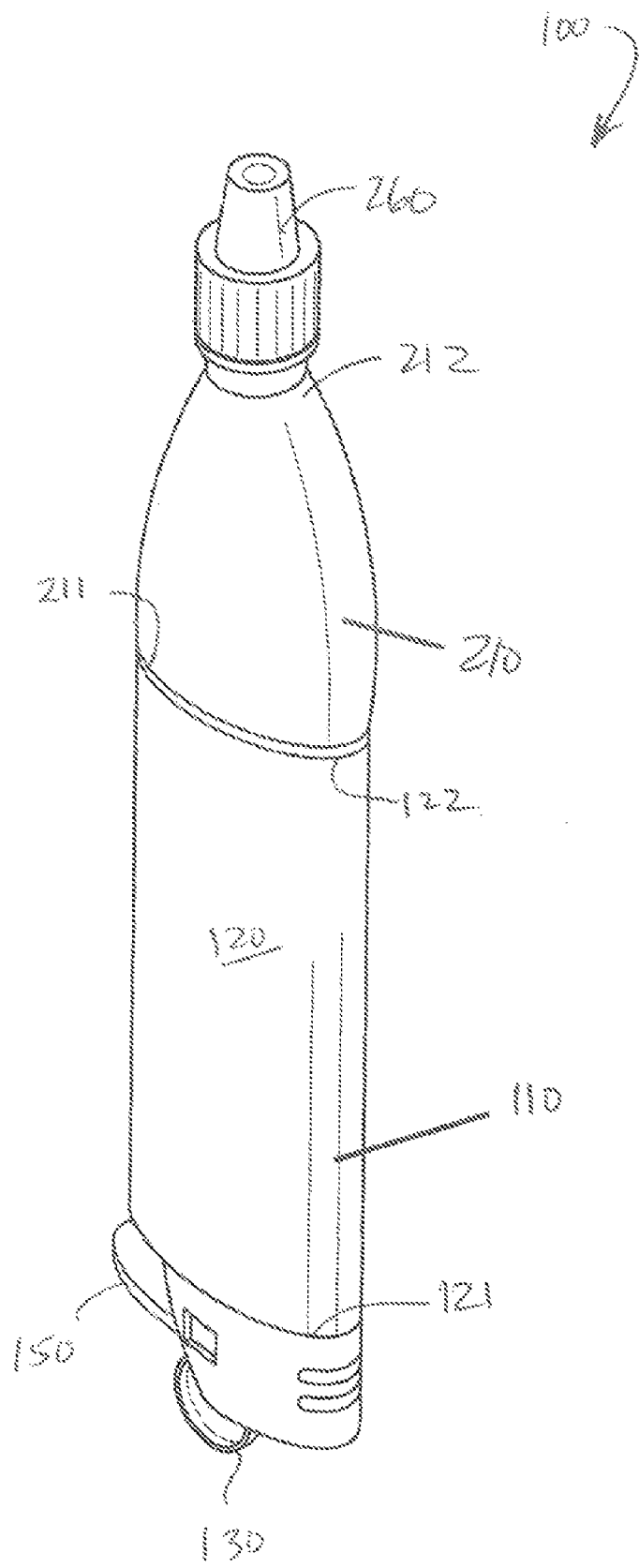
FIG. 2 is a bottom perspective view of the cigarette lighter device of the present invention.
Figure 3:
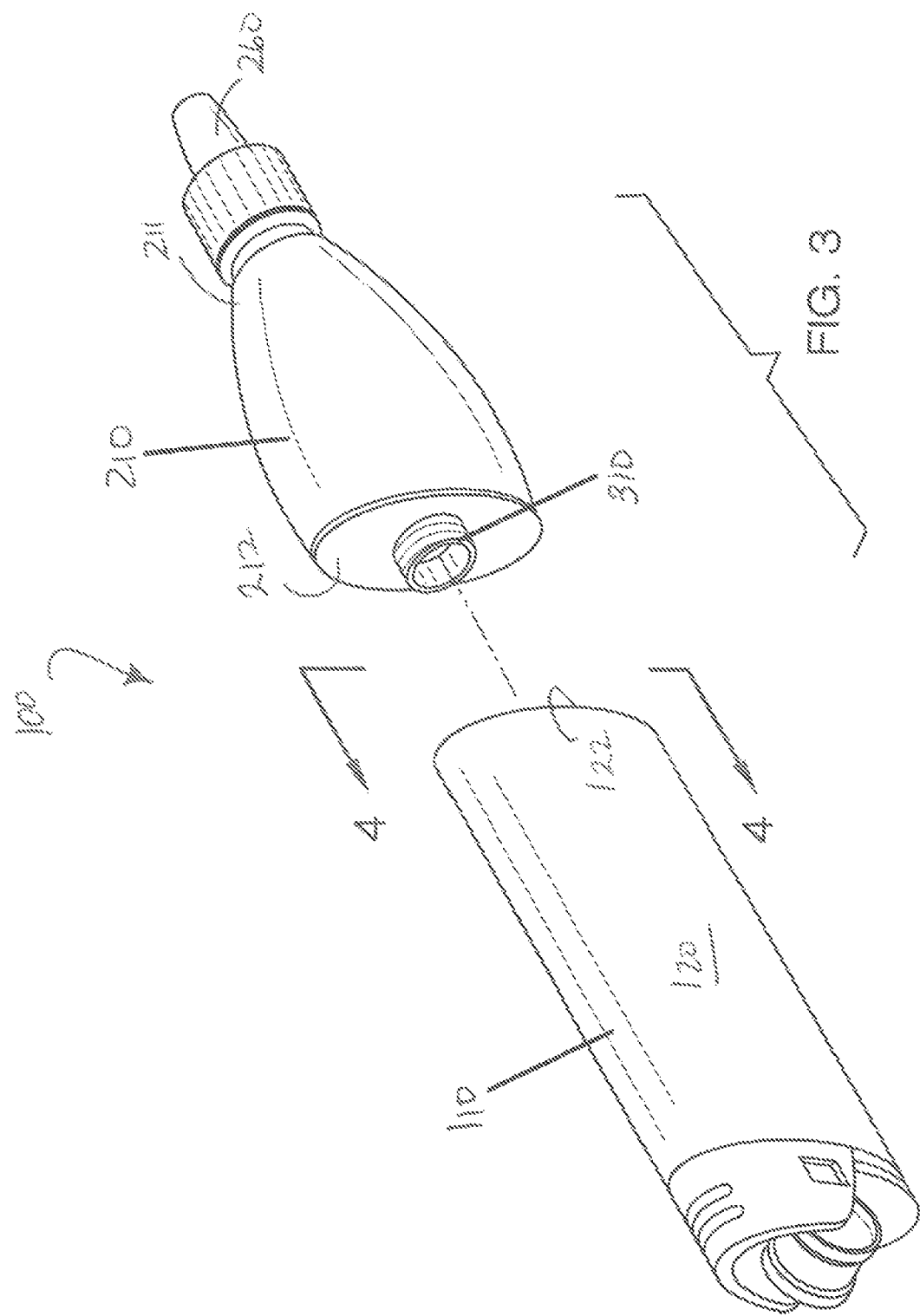
FIG. 3 is a perspective view of the cigarette lighter device of the present invention.
Figure 4:
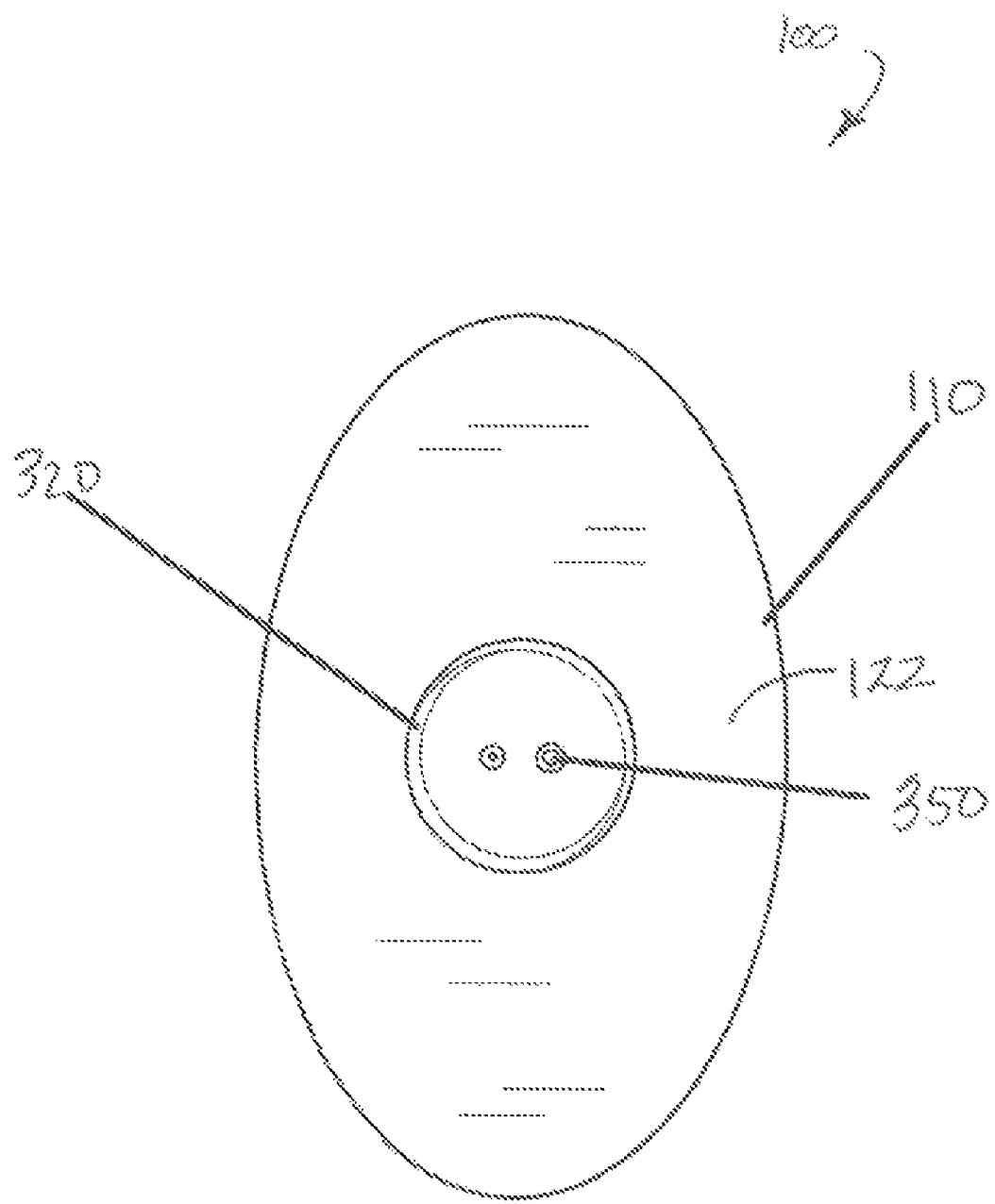
FIG. 4 is a cross sectional view of the cigarette lighter device of the present invention.
Figure 5:
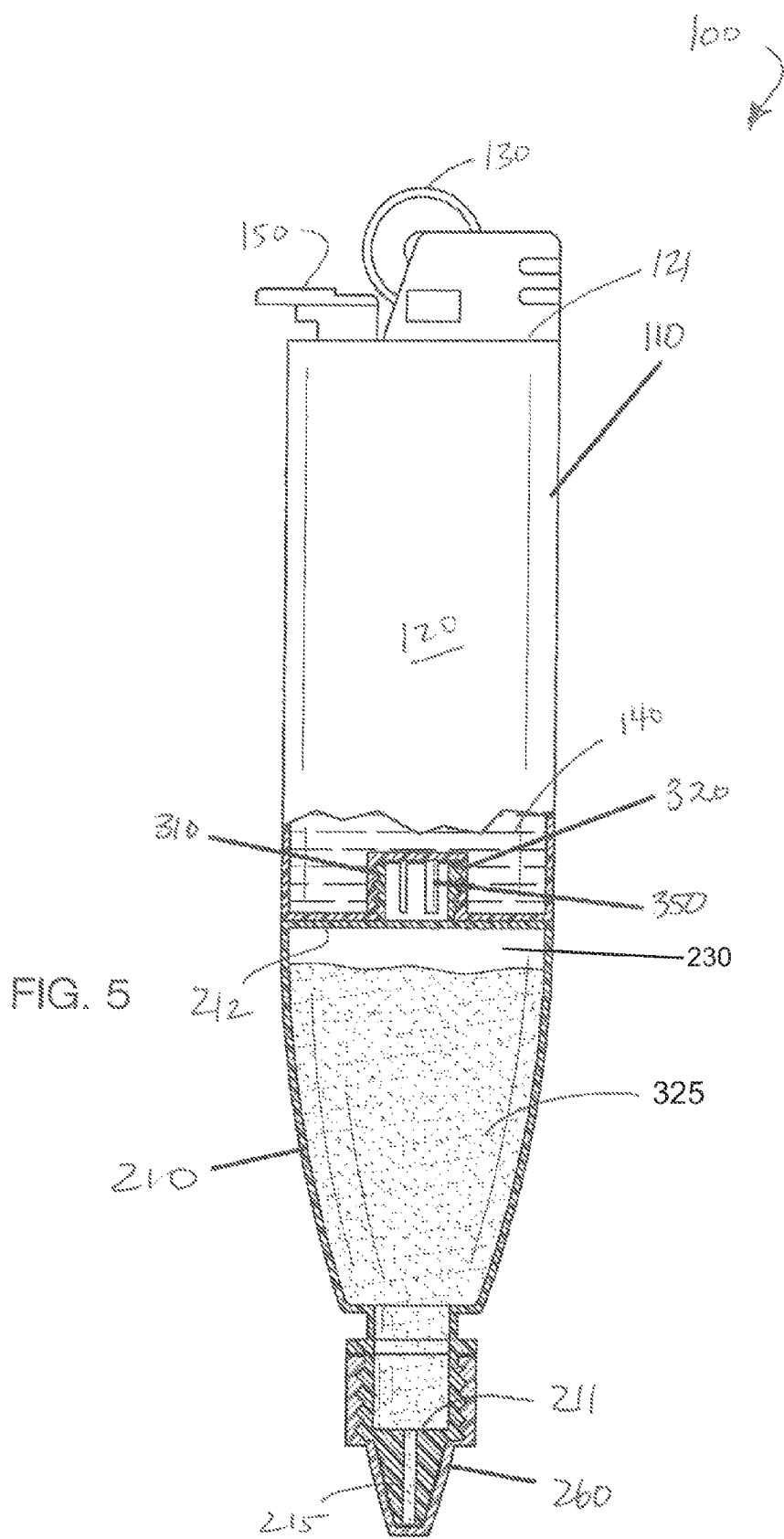
FIG. 5 is a side and internal view of the cigarette lighter device of the present invention.

The following is a listing of numbers corresponding to a particular element refer to herein:
100 cigarette lighter device
110 cigarette lighter component
120 base
121 top end of base
122 bottom end of base
130 flint wheel
140 butane reservoir
150 activation button
210 eye drop dispenser
211 first end of eye drop dispenser
212 second end of eye drop dispenser
215 connecting tube
230 reservoir
325 eye drop fluid
260 cap
310 male threaded component
320 female threaded component
350 refill inlet Referring now to FIGS. 1-5, the present invention features a cigarette lighter device 100 comprising an eye drop dispenser 210. The cigarette lighter device 100 comprises a cigarette lighter component 110, similar to standard disposable cigarette lighters well known to one of ordinary skill in the art. For example, the cigarette lighter component 110 comprises base 120 having a top end 121 and a bottom end 122, a flint wheel 130 disposed at the top end 121, a butane reservoir 140 disposed inside the base 120, and an activation button 150. A user presses his/her finger along the flint wheel 130 while pressing the activation button 150 to light the cigarette lighter component 110.

Disposed at the bottom end 122 of the base 120 is an eye drop dispenser 210 having a first end 211 and a second end 212. Inside the eye drop dispenser 210 is a reservoir 230 for storing eye drop fluid 325.

The eye drop dispenser 210 is removably attached to the cigarette lighter component 110. In some embodiments, a male threaded component 310 is disposed on the second end 212 of the eye drop dispenser 210 which engages a female threaded component 320 disposed on the bottom end 122 of the base 120 of the cigarette lighter component 110, similar to a screw-like mechanism.

The reservoir 230 is fluidly connected to an aperture tip disposed at the first end 211 of the eye drop dispenser 210 via a connecting tube 215. The eye drop fluid 325 can travel from the reservoir 230 through the connecting tube 215 and out of the eye drop dispenser 210. For example, a user can apply pressure (e.g., squeeze) the eye drop dispenser 210 to push the eye drop fluid 325 out of the reservoir 230. In some embodiments, a removable cap 260 is attached to the first end 211 of the eye drop dispenser 210 to prevent eye drop fluid 325 from leaking from the connecting tube 215. If a user needs eye drops, he/she can unscrew the cap 260 and squeeze the eye drop dispenser 210 to push eye drop fluid 325 from the reservoir 230 inside the eye drop dispenser 210.

In some embodiments, the butane reservoir 140 can be refilled with butane after it has been emptied. In some embodiments, a refill inlet 350 is disposed in the bottom end 122 of the base 120 of the cigarette lighter component 110. The refill inlet 350 fluidly connects to the butane reservoir 140. In some embodiments, the eye drop dispenser 210 serves as a cap to the refill inlet 350, preventing butane from leaking out of the refill inlet 350.

The following the disclosures of the following U.S. patents are incorporated in their entirety by reference herein: U.S. Pat. No. 5,366,448; U.S. Pat. No. 4,515,556; U.S. Pat. No. 2,358,955; U.S. Pat. No. 4,583,939; U.S. Pat. No.

U.S. Pat. Application No. 2001/0032652.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A cigarette lighter device comprising:
   (a) a cigarette lighter component having a top end, a bottom end, a flint wheel disposed at the top end, and a butane reservoir disposed inside the cigarette lighter component;
   (b) an eye drop dispenser removably attached to the bottom end of the cigarette lighter component, wherein the eye drop dispenser has a reservoir for storing an eye drop fluid; wherein a male threaded component is disposed on a second end of the eye drop dispenser which is adapted for engaging a female threaded component disposed on the bottom end of the cigarette lighter component;
(c) a connecting tube fluidly connecting the reservoir for storing an eye drop fluid to an aperture tip disposed at a first end of the eye drop dispenser; wherein the eye drop fluid is squeezed from the reservoir out of the eye drop dispenser
(d) a removable cap attached to the first end of the eye drop dispenser for temporarily preventing eye drop fluid from unintentionally exiting the eye drop dispenser.

2. The cigarette lighter device of claim 1, wherein the butane reservoir is refilled with butane after it has been emptied.

3. The cigarette lighter device of claim 2, wherein a refill inlet is disposed in the bottom end of the cigarette lighter component that fluidly connects to the butane reservoir.

4. The cigarette lighter device of claim 3, wherein the eye drop dispenser serves as a cap to the refill inlet.

* * * * *